United States Patent
Huang et al.

(10) Patent No.: US 10,111,440 B2
(45) Date of Patent: Oct. 30, 2018

(54) NON-AQUEOUS, NON-OIL LIVE MICROBIAL COMPOSITIONS

(71) Applicant: Valent BioSciences LLC, Libertyville, IL (US)

(72) Inventors: Zhengyu Huang, Buffalo Grove, IL (US); Benjamin A. Belkind, Wilmette, IL (US); Bala N. Devisetty, Wilmette, IL (US); Venkat Gangavarapu, Vernon Hills, IL (US); Zuoxing Zheng, Buffalo Grove, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

(21) Appl. No.: 15/612,391

(22) Filed: Jun. 2, 2017

(65) Prior Publication Data

US 2017/0347665 A1    Dec. 7, 2017

Related U.S. Application Data

(60) Provisional application No. 62/345,430, filed on Jun. 3, 2016.

(51) Int. Cl.
*A01N 63/00* (2006.01)
*A01N 63/04* (2006.01)
*A01N 25/04* (2006.01)

(52) U.S. Cl.
CPC ............. *A01N 63/04* (2013.01); *A01N 25/04* (2013.01); *A01N 63/00* (2013.01)

(58) Field of Classification Search
CPC ...................................... A01N 63/04
See application file for complete search history.

(56) References Cited

U.S. PATENT DOCUMENTS

| | | | |
|---|---|---|---|
| 5,759,486 A * | 6/1998 | Peterson | A61L 2/12 219/687 |
| 2015/0031544 A1 * | 1/2015 | Harel | A61K 9/1623 504/367 |

OTHER PUBLICATIONS

Mugnier et al (Applied and Environmental Microbiology vol. 50, No. 1, pp. 108-114) (Year: 1985).*
Maddox et al (J. Euk. Microbiol. vol. 43, No. 3, pp. 221-225) (Year: 1996).*

* cited by examiner

*Primary Examiner* — Albert M Navarro
(74) *Attorney, Agent, or Firm* — Wood, Phillips, Katz, Clark & Mortimer

(57) ABSTRACT

The present invention is directed to non-aqueous, non-oil liquid compositions comprising live microbial organisms and a liquid carrier. The present invention is further directed methods of controlling pests comprising applying an effective amount of a non-aqueous, non-oil liquid composition comprising live microbial organisms and a liquid carrier to an area in need of pest control.

13 Claims, No Drawings

NON-AQUEOUS, NON-OIL LIVE MICROBIAL COMPOSITIONS

FIELD OF THE INVENTION

The present invention is directed to non-aqueous, non-oil liquid compositions comprising live microbial organisms and a liquid carrier and methods of their use.

BACKGROUND OF THE INVENTION

Microbial pesticides utilize live microbial organisms as the active ingredient and are used to control a variety of crop pests. For example, downy mildew disease, which attacks the leaves of grapes, vine vegetables, hops and soybeans, is controlled by the use of *Bacillus subtilis*. Further examples include: white mold is controlled by the use of *Coniothyrium minitans*; charcoal rot in curcubits is controlled by the use of *Bacillus amyloliquefacinens*, and parasitic nematodes are controlled by the use of *Paecilomyces lilacinus*.

However, despite the relative high number of patents for microbial pesticides, only a few of them are approved for agricultural use. One of the problems in creating useful microbial pesticide compositions is that they must be formulated to retard the growth of the microbe while maintaining its viability over long periods of storage and be readily diluted or added to various application types.

Previous and current liquid microbial pesticides are aqueous based suspension formulations, such as the commercially available Poncho®/VOTiVO® and DoubleNickle LC and those disclosed in US 2011/0033436A1, assigned to Bayer Intellectual Property GmbH, which is directed to aqueous formulations of various spore forming bacteria and fungi. However, aqueous based formulations are problematic due to the volatile nature of water and the need for harsh preservatives. Further, aqueous based formulations are not compatible with other non-aqueous agricultural products, which presents difficulty in applying the microbial pesticide.

Thus, there is a need in the art for non-aqueous compositions containing live microbial organisms. Preferably these compositions may be readily diluted and are capable of being mixed with a variety of other pesticides. Further these compositions should be capable of controlling pests.

SUMMARY OF THE INVENTION

The present invention is directed to non-aqueous, non-oil liquid compositions comprising live microbial organisms and a liquid carrier.

The present invention is further directed to methods of controlling pests comprising applying an effective amount of a non-aqueous, non-oil liquid composition comprising live microbial organisms and a liquid carrier to an area in need of pest control.

DETAILED DESCRIPTION OF THE INVENTION

Applicants unexpectedly discovered that non-aqueous, non-oil liquid compositions containing a liquid carrier provide superior stability and viability of live microbial organisms. This finding was unexpected because it was previously unknown whether non-aqueous, non-oil liquid compositions could be used for storage and dispersal of microbial organisms.

In one embodiment the present invention is directed to non-aqueous, non-oil liquid compositions comprising live microbial organisms and a liquid carrier.

In a preferred embodiment the live microbial organisms are dormant.

In another preferred embodiment the live microbial organisms are bacteria.

In a more preferred embodiment the bacteria are selected from the group consisting of *Bacillus thuringiensis*, *Bacillus papillae*, *Bacillus lentimorbus*, *Bacillus sphaericus*, *Paenibacillus popilliae*, *Serratia entomophila* and *Xanthomonas campestris Bacillus pumilus*, *Pseudomonas* spp, *Streptomyces griseoviridis* and *Burkholderia cepacia*. *Bacillus firmus*, *Pasteuria penetrans* and *Bradyrhizobium* spp.

In an even more preferred embodiment the *Bacillus thuringiensis* are selected from the group selected from *kurstaki*, *israelensis*, *tenebrinos entomocidus*, *galleriae* and *aizawai*.

In another preferred embodiment the live microbial organisms are fungi.

In a more preferred embodiment the fungi are selected from the group consisting of *Beauveria bassiana*, *Lagenidum giganteum*, *Metarhizium anisopliae*, *Entomophaga*, *Zoopthora*, *Paecilomyces fumosoroseus*, *Normuraea*, *Lecanicillium lecanii Colletotrichum gloeosporioides*, *Chondrostereum purpureum*, *Cylindrobasidium laeve*, *Ampelomyces quisqualis*, *Candida* spp., *Clonostachys rosea f. catenulate*, *Coniothyrium minitans*, *Pseudozyma flocculosa*, *Trichoderma* spp. *Myrothecium verrucaria*, *Paecilomyces lilacinus* and *Mycorrhizae fungi* such as *Glomeromycota* and *Basidiomycota*.

In another preferred embodiment the live microbial organisms are protists.

In a more preferred embodiment the protists are selected from the group consisting of *Nosema locustae*, *Thelohania* and *Vairimorpha*.

In another preferred embodiment the composition is in the form of a suspension concentrate.

In a preferred embodiment the liquid carrier is selected from the group consisting of a polyethylene glycol, glycerol, ethylene glycol, dipropylene glycol, propylene carbonate and mixtures thereof, more preferably a mixture of a polyethylene glycol and glycerol.

In another embodiment the present invention is directed to non-aqueous, non-oil liquid compositions comprising live microbial organisms, a liquid carrier, a vinylpyrrolidone polymer and a nonionic block copolymer.

In another preferred embodiment the liquid carrier is at a concentration from about 15% to about 99% w/w.

In another preferred embodiment the concentration of the live microbial organisms is from about 1% to about 50% w/w.

In another embodiment the present invention is directed to non-aqueous, non-oil liquid compositions comprising live microbial organisms, a liquid carrier and at least one adjuvant selected from the group consisting of surfactants, suspension aids, rheology modifiers, stickers, dispersants, stabilizers and preservatives.

In another embodiment the present invention is directed to non-aqueous, non-oil liquid compositions comprising:
  i) live microbial organisms; and
  ii) a liquid carrier comprising a mixture of a polyethylene glycol and glycerol.

In another embodiment the present invention is directed to non-aqueous, non-oil liquid compositions comprising:
  i) live microbial organisms at a concentration from about 20% to about 30% w/w;

ii) a polyethylene glycol at a concentration from about 70% to about 80% w/w; and iii) glycerol is at a concentration from about 5% to about 10% w/w.

In another embodiment the present invention is directed to non-aqueous, non-oil liquid compositions comprising:

i) live microbial organisms at a concentration from about 20% to about 30% w/w;

ii) a polyethylene glycol at a concentration from about 70% to about 80% w/w;

iii) glycerol at a concentration from about 5% to about 10% w/w;

iv) a vinylpyrrolidone polymer at a concentration from about 0.1% to about 5% w/w; and v) a nonionic block copolymer at a concentration from about 0.1% to about 5% w/w.

In another embodiment the present invention is directed to a method of controlling pests comprising applying an effective amount of a composition of the invention to an area in need of pest control.

In another embodiment, the compositions of the present invention may be applied at a rate of from about 5 to about 400 grams of live microbial organisms per hectare, preferably from about 10 to about 300 grams per hectare and more preferably from about 25 to about 300 grams per hectare.

In another embodiment, the compositions of the present invention may be applied at a rate of from about 0.01 to about 100 milligrams of live microbial organisms per 100,000 seeds or 100 pounds of seed, preferably from about 0.1 to about 10 milligrams of live microbial organisms per 100,000 seeds or 100 pounds of seed and more preferably from about 0.3 to about 3 milligrams of live microbial organisms per 100,000 seeds or 100 pounds of seed.

In a preferred embodiment the area in need of pest control is plant propagation material.

In a more preferred embodiment the plant propagation material is seeds.

Compositions of the present invention may be applied to any plant in need of pest control, including but not limited to, landscape plants, fruits trees, nut trees, fruit vines, vegetable crops and cereal crops.

In another preferred embodiment the area in need of pest control is an area where crops are grown.

In a more preferred embodiment the crops are selected from the group consisting of soybean, corn, potato, and cereal crops.

In another embodiment, the present invention is directed to methods of improving plant growth comprising applying a composition of the present invention to a plant, plant propagation material or an area where a plant will grow, preferably soil and more preferably a furrow or a plant root zone.

In another embodiment, the composition of the present invention can be applied with an herbicide such as glyphosate, mesotrione, halosulfuron, saflufenacil or dicamba.

In another embodiment, the composition of the present invention can be applied with a fungicide such as tetraconazole, metconazole, a strobilurin, or a combined strobilurin-azole product.

In another embodiment, the composition of the present invention can be applied with an insecticide such as methylparathion, bifenthryn, esfenvalerate, lorsban, carbaryl or lannate.

In yet another embodiment, compositions of the invention can be applied with foliar fertilizers such as CoRoN (available from Helena Chemical), a controlled-release nitrogen, or BioForge (available from Stoller USA), which is largely N,N'-diformyl urea, or other micro nutrient-containing sprays.

The compositions of the present invention can be applied by any convenient means. Those skilled in the art are familiar with the modes of application that include foliar applications such as spraying and soil applications including spraying, in-furrow treatments, or side-dressing.

In another embodiment the present invention is directed to a method of improving plant growth comprising applying an effective amount of a composition of the invention to a plant or plant propagation material.

As used herein, the term "live" refers to an organism that can grow and replicate.

As used herein, the term "dormant" refers to a stage in the life cycle of a live organism in which the growth and replication of the organism is suspended or retarded.

As used herein, the term "plant propagation material" refers to seeds of all kinds (fruit, tubers, grains), cuttings, cut shoots and the like.

As used herein, the term "microbial organism" or "microbial organisms" refers to microscopic organisms including unicellular and multicellular organisms including unicellular organisms that form cell clusters. Microbial organisms include, but are not limited to, bacteria, archaebacteria, fungi, protists, and algae.

As used herein the term "effective amount" refers to an amount of a live microbial organism capable of providing control of a nematode.

As used herein, "control" or "controlling" refers to killing or inhibiting, slowing or preventing the growth and/or propagation of an organism.

As used herein, "improving" means that the plant has more of the specific quality than the plant would have had it if it had not been treated by methods of the present invention.

As used herein, "suspension concentrate" refers to a formulation wherein insoluble particles are suspended in liquid diluents. A suspension concentrate is not a solution.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

As used herein % w/w denotes weight by total weight of the composition. All concentrations listed herein are in % w/w unless otherwise described.

Liquid carriers suitable for use in the present invention include, but are not limited to, triacetin, polyethylene glycols (such as PEG 300, PEG 400,), polysorbates (such as Polysorbate 20, Polysorbate 40, Polysorbate 60, Polysorbate 65, or Polysorbate 80), Poloxamers (such as Poloxamer 124, Poloxamer 188, Poloxamer 237, Poloxamer 338, or Poloxamer 407), polyoxyethylene ethers (such as Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether), polyoxyethylated alkylphenols, copolymer of alkylphenol epoxyethane and epoxypropane, polyoxylstearates (such as Polyoxyl 30 stearate, Polyoxyl 40 stearate, Polyoxyl 50 stearate, Polyoxyl 100 stearate), polyethoxylated stearates (such as a polyethoxylated 12-hydroxy stearate), N-methyl pyrrolidone, propylene glycol, ethyl acetate, lactic acid esters, esters of carbonic acid such as propylene carbonate, dimethyl sulfoxide, dimethyl acetamide, benzyl alcohol, 2-pyrrolidone, benzyl benzoate, $C_{2-6}$ alkanols, 2-ethoxyethanol, alkyl esters such as 2-ethoxyethyl acetate, methyl acetate, ethyl acetate, ethylene glycol diethyl ether, ethylene glycol dimethyl ether, acetone, glycerol, alkyl ketones such as methylethyl ketone and dimethyl sulfone, tetrahydrofuran, cyclic alkyl amides such as caprolactam, decylmethylsulfoxide, C1-C4 dialkyl amides of C1-C18 carboxylic acids, such as dimethyl amide of octanoic acid, N-alkyl pyrrolidones such as N-methyl-2-pyrrolidone, and Tributyrin, polyalkyleneoxide modified heptamethyltrisiloxane and mixtures thereof. Preferred liquid carriers include polyethylene glycols, glycerol, ethylene glycol, dipropylene glycol, propylene carbonate or mixtures thereof, more preferably a mixture of a polyethylene glycol and glycerol. In a preferred embodiment the liquid carrier is included in the composition at a concentration from about 15% to about 99% w/w.

Polyethylene glycols are compounds containing a repeating subunit of the following molecular structure H—(O—CH$_2$—CH$_2$)$_n$—OH. Polyethylene glycols are identified based on their average molecular weight. For example, a polyethylene glycol with an average molecular weight of 400 daltons is named polyethylene glycol 400. In a preferred embodiment, the polyethylene glycol has an average molecular weight from about 100 to about 800 daltons.

The compositions utilized in the methods of the present invention can be formulated to contain additional adjuvants, such as:

anti-caking agents, including but not limited to, sodium phosphate, ammonium phosphate, sodium acetate, sodium metasilicate, magnesium, zinc and calcium sulfate, magnesium hydroxide, anhydrous calcium chloride, sodium alkylsulfosuccinates, calcium and barium oxides;

stabilizers, including but not limited to, epoxidized animal or vegetable oils, such as epoxidized soybean oil;

defoamers, including but not limited to, silicone antifoam agents and lower polyoxyethylene and polyoxypropylene block polymers (wherein the number of octyl-, nonly- and phenylpolyoxyethylene/ethylene oxide units is >5) and long-chain alcohols;

slip agents, including but not limited to, fatty amines, oleamides, and erucamides;

dispersants, including but not limited to, Agrimer® 30 (vinylpyrrolidone polymer; Agrimer is a registered trademark of ISP Investment, Inc. and is available from Ashland), polyethylene glycol/polypropylene glycol block copolymers, Atlox® 4912 (nonionic block copolymer; Atlox is a registered trademark of and available from Croda Americas LLC), polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers including the alkali metal, alkaline earth metal, ammonium and amine salts thereof, preferably the dispersant is a vinylpyrrolidone polymer, a nonionic block copolymer or a combination thereof, more preferably the dispersant is a combination of from about 0.1% to about 5% w/w of a vinylpyrrolidone polymer and from about 0.1% to about 5% w/w a nonionic block copolymer;

rheology modifiers, including but not limited to, Attagel 50 (magnesium aluminum phyllosilicate), clays and organoclays, hydrophilic and hydrophobic silicas, hydrogenated castor oils and their derivatives, polyamides, microcrystalline cellulose, oxidized waxes and steric dispersants (e.g., comb polymers such as polyvinylpyrrolidinones or polyacrylates), preferably the rheology modifier is magnesium aluminum phyllosilicate, more preferably at a concentration from about 0.1% to about 5% w/w;

wetting agents, including but not limited to, naphthalenesulfonic acids including their alkali metal, alkaline earth metal, ammonium and amine salts, fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters;

thickening agents, including but not limited to, hydrated fumed silica or attapulgite clays or amine treated attapulgite clays;

emulsifiers, including but not limited to, polyoxyethylene alkyl aryl ester sulfate and polyoxyethylene styryl aryl ether sulfate, alkoxylated alcohols, ethoxylated alcohols, ethopropoxylated alcohols, alkylphenolethoxylates, alkoxylated tristyrylphenols, alkoxylated tributylphenols, alkylaminethoxylates, ethoxylated vegetable oils including their hydrogenates, polyadducts of ethylene oxide and propylene oxide (e.g. polyoxyethylene-polyoxypropylene block copolymers and their derivatives), ethoxylated fatty acids, nonionic polymeric surfactants (e.g. polyvinylalcohol, polyvinylpyrrolidone, polymethacrylates and their derivatives), sorbitan esters and their ethoxylates, sorbitolesters, propylene glycol esters of fatty acids and polyglycerolesters;

preservatives, including but not limited to, 1,2-benzisothiazolin-3-one based preservatives, 5-chloro-2-methyl-2H-isothiazol-3-one preservatives, and 2-methyl-2H-isothiazol-3-one preservatives, which increase the long lasting activity of the actives; and Silwet® ECO (polyalkyleneoxide modified heptamethyltrisiloxane; Silwet is a registered trademark of and available from Momentive Performance Materials Inc.) Other components that enhance the biological activity or application of these ingredients may optionally be included.

These representative embodiments are in no way limiting and are described solely to illustrate some aspects of the invention.

Further, the following examples are offered by way of illustration only and not by way of limitation.

EXAMPLES

Example 1

Concentrated 22.5% *Bacillus amyloliquefaciens* Suspension Formulations

TABLE 1

| Formulation #1 | % w/w |
|---|---|
| Polyethylene glycol | To 100% |
| Glycerol | 7 |
| Silwet ® ECO | 0.5 |
| (Polyalkyleneoxide modified Heptamethyltrisiloxane) | |
| Agrimer ® 30 | 1.5 |
| (Vinylpyrrolidone polymer) | |

TABLE 1-continued

| Formulation #1 | % w/w |
|---|---|
| Atlox ® 4912 (Nonionic block copolymer) | 1 |
| Tech powder of *Bacillus amyloliquefaciens* (Strain BA-1) | 22.5 |

TABLE 2

| Formulation #2 | % w/w |
|---|---|
| Polyethylene glycol | To 100% |
| Glycerol | 7 |
| Silwet ® ECO (Polyalkyleneoxide modified Heptamethyltrisiloxane) | 0.5 |
| Attagel ™ 50 (magnesium aluminum phyllosilicate) | 3.1 |
| Agrimer ® 30 (Vinylpyrrolidone polymer) | 0.1 |
| Tech powder of *Bacillus amyloliquefaciens* (Strain BA-1) | 22.5 |

Example 2

Viability Studies

Applicants tested the viability of *Bacillus amyloliquefaciens* in the formulations of Example 1. This study was conducted using standard procedures known and accepted by those of skill in the art. The results of this study can be seen below in Tables 3 and 4.

TABLE 3

| Formulation #1 | # of Colony Forming Units | |
|---|---|---|
| Temperature | 0 Months | 9 Months |
| 5° C. | $8.2 \times 10^{10}$ | $8.13 \times 10^{10}$ |
| 25° C. | $8.2 \times 10^{10}$ | $7.63 \times 10^{10}$ |
| 30° C. | $8.2 \times 10^{10}$ | $8.36 \times 10^{10}$ |

TABLE 4

| Formulation #2 | # of Colony Forming Units | |
|---|---|---|
| Temperature | 0 Months | 3 Months |
| 5° C. | $7.4 \times 10^{10}$ | $7.45 \times 10^{10}$ |
| 25° C. | $7.4 \times 10^{10}$ | $9.10 \times 10^{10}$ |
| 30° C. | $7.4 \times 10^{10}$ | $7.58 \times 10^{10}$ |
| tropical 25-40° C. | $7.4 \times 10^{10}$ | $8.50 \times 10^{10}$ |

As can be seen in Tables 3 and 4, the compositions of Example 1 provide stability and viability of *Bacillus amyloliquefaciens*. Specifically, neither formulation allowed for a significant reduction in the number of colony forming units when stored at various temperatures for an extended time period. The number of colony forming units is a measure of viability as each colony forming unit represents an individual *Bacillus amyloliquefaciens* organism that was able to grow and propagate. Thus, the compositions of Example 1 are capable of providing long-term, stable storage of live microbial organisms while maintaining viability.

Example 3

Concentrated *Mycorrhizae* Suspension Formulations

TABLE 5

| Formulation #1 | % w/w |
|---|---|
| Polyethylene glycol 200 | To 100% |
| Garamite ® 1958 (alkyl quaternary ammonium clay) | 2.5 |
| Silwet ® ECO (Polyalkyleneoxide modified Heptamethyltrisiloxane) | 0.5 |
| Agrimer ® 30 (Vinylpyrrolidone polymer) | 1.5 |
| Tween ® 20 (Polysorbate 20) | 3.0 |
| Jeffsol ® AG 1555 (1,2-propanediol cyclic carbonate) | 1 |
| Tech powder of *Mycorrhizae* | 8.7 |

TABLE 6

| Formulation #2 | % w/w |
|---|---|
| Polyethylene glycol 200 | To 100% |
| Garamite ® 1958 (alkyl quaternary ammonium clay) | 3.0 |
| Silwet ® ECO (Polyalkyleneoxide modified Heptamethyltrisiloxane) | 0.5 |
| Agrimer ® 30 (Vinylpyrrolidone polymer) | 1.5 |
| Tween ® 20 (Polysorbate 20) | 3.0 |
| Jeffsol ® AG 1555 (1,2-propanediol cyclic carbonate) | 2.0 |
| Tech powder of *Mycorrhizae* | 1.5 |

What is claimed is:

1. A non-aqueous, non-oil liquid composition comprising live microbial organisms, a liquid carrier selected from the group consisting of a polyethylene glycol, glycerol, ethylene glycol, dipropylene glycol, propylene carbonate and mixtures thereof, a vinylpyrrolidone polymer and a nonionic block copolymer.

2. The composition of claim 1, wherein the live microbial organisms are bacteria.

3. The composition of claim 1, wherein the live microbial organisms are fungi.

4. The composition of claim 1, wherein the composition is in the form of a suspension concentrate.

5. The composition of claim 1, wherein the liquid carrier is a mixture of a polyethylene glycol and glycerol.

6. The composition of claim 1, wherein the liquid carrier is at a concentration from about 15% to about 99% w/w, wherein w/w denotes weight by total weight of the composition.

7. The composition of claim 1, further comprising at least one adjuvant selected from the group consisting of surfactants, suspension aids, rheology modifiers, stickers, dispersants, stabilizers and preservatives.

8. The composition of claim 1, wherein the concentration of the live microbial organisms is from about 1% to about 50% w/w, wherein w/w denotes weight by total weight of the composition.

9. A non-aqueous, non-oil liquid composition comprising:
  i) live microbial organisms at a concentration from about 20% to about 30% w/w; and
  ii) a liquid carrier comprising a mixture of from about 5% to about 94% w/w of a polyethylene glycol and from about 5% to about 10% w/w glycerol,
wherein w/w denotes weight by total weight of the composition.

10. The composition of claim 9, further comprising:
  i) a vinylpyrrolidone polymer at a concentration from about 0.1% to about 5% w/w; and
  ii) a nonionic block copolymer at a concentration from about 0.1% to about 5% w/w.

11. A method of controlling pests comprising applying an effective amount of the composition of claim 1 to an area in need of pest control.

12. The method of claim 11, wherein the area in need of pest control is an area where crops are grown.

13. A method of improving plant growth comprising applying an effective amount of the composition of claim 1 to a plant, plant propagation material or an area where a plant will grow.

\* \* \* \* \*